(12) United States Patent
Spector et al.

(10) Patent No.: US 6,268,374 B1
(45) Date of Patent: Jul. 31, 2001

(54) URACIL REDUCTASE INACTIVATORS

(75) Inventors: Thomas Spector, Durham; David J. T. Porter, Raleigh, both of NC (US); Saad G. Rahim, Beckenham (GB)

(73) Assignee: Glaxo Wellcome Inc., Research Triangle Park, NC (US)

( * ) Notice: Subject to any disclaimer, the term of this patent is extended or adjusted under 35 U.S.C. 154(b) by 0 days.

(21) Appl. No.: 08/030,259

(22) PCT Filed: Sep. 25, 1991

(86) PCT No.: PCT/GB91/01650

§ 371 Date: Jul. 23, 1993

§ 102(e) Date: Jul. 23, 1993

(87) PCT Pub. No.: WO92/04901

PCT Pub. Date: Apr. 2, 1992

(51) Int. Cl.$^7$ .......................... A61K 31/70; A61K 31/505
(52) U.S. Cl. .............. 514/274; 514/49; 514/50; 514/256; 536/28.2; 536/28.54; 544/309; 544/313
(58) Field of Search .................. 514/49, 50, 256, 514/274; 536/28.2, 28.54; 544/309, 313

(56) References Cited

U.S. PATENT DOCUMENTS

| | | | |
|---|---|---|---|
| 4,124,765 | 11/1978 | Kurono et al. | 544/313 |
| 4,381,344 | 4/1983 | Rideout et al. | 435/87 |
| 4,719,214 | 1/1988 | Shealy | 514/274 |
| 4,863,927 | 9/1989 | Tolman et al. | 514/274 |
| 5,643,913 | * 7/1997 | Spector et al. | 514/274 |

FOREIGN PATENT DOCUMENTS

| | | |
|---|---|---|
| 2522369C2 | 11/1988 | (DE) . |
| 0 272 065A2 | 6/1988 | (EP) . |
| 0 337 599A1 | 10/1989 | (EP) . |
| 0 356 166 A2 | 2/1990 | (EP) . |
| 0 371 139A1 | 6/1990 | (EP) . |
| 0 409 575A1 | 1/1991 | (EP) . |
| 92/01452 | 2/1992 | (WO) . |

OTHER PUBLICATIONS

International Search Report and Annex thereto for International Application No. PCT/GB91/01650 mailed Jan. 8, 1992.

Parker, W. B. et al., "Metabolism and Mechanism of Action of 5–Fluorouracil", *Pharmacol. and Ther.*, 48, 381–395 (1990).

Fardos N.M. Naguib et al., "Structure–Activity Relationship of Ligands of Dihydrouracil Dehydrogenase from Mouse Liver", *Biochemical Pharmacology*, 38(9), 1471–1480 (1989).

Masaaki Iigo et al., "Enhancing Effect of Bromovinyldeoxyuridine on Antitumor Activity of 5'–Deoxy–5–Fluorouridine Against Adenocarcinoma 755 in Mice", *Biochemical Pharmacology*, 38(12), 1885–1889 (1989).

Thornburg, Lora D. et al., "Mechanism–Based Inhibition of Thymine Hydroxylase", *J. American Chemical Society*, 111, 7632–7633 (1989).

Kunihiko Tatsumi et al., "Inhibitory Effects of Pyrimidine, Barbituric Acid and Pyridine Derivatives on 5–Fluorouracil Degradation in Rat Liver Extracts", *Japan. J. Cancer Research (Gann)*, 78, 748–755 (1987) (cited in European Search Report).

Tuchman, M. et al., *Chemical Abstracts*, 104:14633m (1986) (cited in European Search Report).

Desgranges, C. et al., "Effect of (E)–5–(1–Bromovinyl)uracil on the Catabolism and Antitumor Activity of 5–Fluorouracil in Rats and Leukemic Mice", *Cancer Research*, 46, 1094–1101 (1986).

Ho, D. H. et al., "Distribution and Inhibition of Dihydrouracil Dehydrogenase Activities in Human Tissues Using 5–Fluorouracil as a Substrate", *Anticancer Research*, 6(4), 781–784 (1986).

Fujii, S. et al., "Cancer—chemotherapy with 5–fluorouracil and its derivatives", *Int. Congr. Ser.–Excerpta Med.*, 729 Cancer Chemotherapy: Challenges Future, 117–25 (1986).

Chu, M. Y. W. et al., "Potentiation of 5 Fluoro–2'–Deoxy Uridine Anti Neoplastic Activity by the Uridine Phosphorylase Benzyl Acyclo Uridine and Benzyloxybenzyl Acyclo Uridine", *Cancer Research*, 44(5), 1852–1856 (1984).

Farkaš, Jiří, "Synthesis of 1,2,4–Triazine–3,5(2H,4H)–Diones Containing Electronegative Substituents in Position 6", *Collection Czechoslovak Chem. Commun.*, 48(9), 2676–2681 (1983).

Robins, Morris J. et al., "Nucleic Acid Related Compounds. 39. Efficient Conversion of 5–Iodo to 5–Alkynyl and Derived 5–Substituted Uracil Bases and Nucleosides", *J. Organic Chemistry*, 48(11), 1854–62(1983).

Kundu, Nitya G. et al., "Studies on Uracil Derivatives and Analogs. Syntheses of 5–(β–Trimethylsilyl)ethynyluracil and 5–Ethynyluracil", *J. Heterocyclic Chem.*, 19(3), 463–4(1982).

Robins, Morris J. et al., "Nucleic Acid Related Compounds. 38. Smooth and high–yield iodination and chlorination at C–5 of uracil bases and p–toluyl–protected nucleosides", *Canada J. Chemistry*, 60(5), 554–7(1982).

(List continued on next page.)

*Primary Examiner*—Peter O'Sullivan
(74) *Attorney, Agent, or Firm*—John L. Lemanowicz (57) ABSTRACT

The present invention relates to a group of 5-substituted uracil derivatives which are inactivators of uracil reductase and which are particularly useful in cancer chemotherapy, especially in combination with antimetabolite antineoplastic agents such as 5-fluorouracil.

19 Claims, 2 Drawing Sheets

OTHER PUBLICATIONS

Barr, Philip J. et al., "Synthesis of Some 5–Halogenovinyl Derivatives of Uracil and their Conversion into 2'–Deoxyribonucleosides", *J. Chemical Society Perkin Trans.,* 1(16), 1665–70(1981).

Krenitsky, T.A. et al., "Purine Nucleoside Synthesis, an Efficient Method Employing Nucleoside Phosphorylases", *Biochemistry,* 20 3615–3621(1981).

Robins, Morris J. et al., "Nucleic Acid Related Compounds. 31. Smooth and Efficient Palladium–Copper Catalyzed Coupling of Terminal Alkynes with 5–Iodouracil Nucleosides", *Tetrahedron Let,* 22(5), 421–4(1981).

Bleackley, R.C. et al., "Replacement of the Iodine Atom of 5–Iodouracil by the 5–Cyano Group", *Nucleic Acid Chemistry,* vol. 2,927–30(1978).

Hein, L. et al., Preparation of 5–Trifluoromethyluracil, *Z. Chem.,* 17(11), 415–16 (1977) (Translation).

Barr, P.J. et al., "Incorporation of 5–substituted uracil derivatives into nucleic acids. Part IV. The synthesis of 5–ethynyluracil", *Nucleic Acids Research,* 3(10), 2845(1976) (cited in European Search Report).

Jones, A.S. et al., "A method for the rapid preparation of 5–vinyluracil in high yield", *Nucleic Acids Research,* 1(1), 105–7 (1974).

Jones et al. "Synthesis and Antiviral Properties of (2)–5–(2–Bromovinyl)–2'–deoxyuridime", *J Med Chem* (1981) 24, pp. 759–760.*

* cited by examiner

_URACIL REDUCTASE INACTIVATORS_

This is a continuation of application Ser. No. 08/718,481 filed Sep. 26, 1996, which is a 371 of International application No.: PCT/FP95/00900, filed Mar. 9, 1995.

The present invention relates to certain enzyme inactivators which are useful in medicine, particularly cancer chemotherapy, especially in combination with antimetabolite antineoplastic agents such as 5-fluorouracil (5-FU).

5-Fluorouracil has been used in cancer chemotherapy since 1957. Sensitive tumours include breast cancer, gastrointestinal malignancies, and cancers of the head and neck; 5-fluorouracil is also used as a radiation sensitiser. 5-Fluorouracil is metabolised rapidly in the liver (half life between about 8 and 20 minutes) by the enzyme dihydropyrimidine dehydrogenase (uracil reductase). It has been reported (Cancer Research 46, 1094, 1986) that 5-(2-bromovinyl)-uracil (BVU) is an inhibitor of dihydrothymidine dehydrogenase which both retards the metabolism of 5-fluorouracil and enhances its antitumour activity. It has been reported that 5-(2-bromovinyl)-2'-deoxyuridine (which is metabolised in vivo to BVU) enhances the antitumour activity of 5-fluorouracil and 5-deoxy-5-fluorouridine, a prodrug of 5-fluorouracil (Biochemical Pharmacology 38; 2885, (1989)).

Unfortunately BVU is toxic to humans.

It has now been discovered that a group of 5-substituted uracil derivatives are inactivators of uracil reductase; they increase the level and half life of 5-fluorouracil in plasma and enhance the activity of 5-fluorouracil. They also reduce the normally encountered variations of 5-fluorouracil plasma levels between subjects.

Accordingly, in a first aspect, the present invention provides a uracil reductase inactivator which is a 5-substituted- or 5,6-dihydro-5-substituted -uracil derivative, wherein the 5-substituent is bromo, iodo, cyano, halo-substituted $C_{1-4}$ alkyl, $C_{2-6}$ alkenyl, a 1-halo $C_{2-6}$ alkenyl group, a $C_{2-6}$ alkynyl group, a halo-substituted $C_{2-6}$ alkynyl group, or a prodrug thereof, for use in medicine, particularly for use in cancer chemotherapy. The uracil reductase inhibitor will generally be used in conjunction with 5-fluorouracil or a prodrug thereof.

By a $C_{2-6}$ alkynyl group is meant a straight or branched chain alkynyl group, the latter including an alkynyl group substituted by a cycloalkyl group containing between 2 and 6 carbon atoms in total.

The halogen substituent on the alkenyl or alkynyl group is preferably bromo, chloro or iodo. Halo-substituted ethenyl and ethynyl groups are particularly preferred. Usually only one halo substituent will be present.

In a further aspect, the present invention provides a uracil derivative as hereinbefore defined for use in the manufacture of a medicament for use in cancer chemotherapy. The medicament may also be useful for rescue from 5-fluorouracil toxicity; and together with 5-fluorouracil or a prodrug thereof for the treatment of psoriasis or rheumatoid arthritis, or human papilloma virus infections.

In a further aspect, the present invention provides a method for the treatment or prophylaxis of tumours which comprises the administration of an effective amount of uracil derivative as hereinbefore defined in the treatment of tumours in mammals, including man. Preferably the treatment is in combination with 5-fluorouracil or a prodrug thereof.

In a yet further aspect, the present invention provides a combination of a uracil derivative as hereinbefore defined or prodrug thereof, and 5-fluorouracil or a prodrug thereof.

Preferred uracil derivatives are these wherein the 5-substituent is a $C_{2-6}$ alkynyl group (optionally halo-substituted), conveniently a $C_{2-4}$ alkynyl group and preferably an ethynyl or propynyl group. In preferred 1-halo-alkenyl and alkynyl derivatives the multiple bond is in the 1-position. Particularly preferred inactivators of uracil reductase for use in accordance with the invention are 5-ethynyluracil and 5-propynyluracil. Other inactivators for such use include:

5-cyanouracil
5-bromoethynyluracil
5-(1-chlorovinyl)uracil
5-iodouracil
5-hex-1-ynyluracil
5-vinyluracil
5-trifluoromethyluracil
5-bromouracil Uracil derivatives where the 5-substituent is a substituted or unsubstituted $C_{3-6}$ alkynyl group are novel compounds and form a further aspect of the present invention.

Prodrugs of the uracil derivatives hereinbefore defined are compounds which may be metabolised in vivo to give the uracil derivatives. These prodrugs may or may not have activity in their own right but will normally have little activity. Such prodrugs include nucleoside analogues which contain a nucleobase corresponding to the above 5-substituted uracil compounds, for example nucleoside derivatives containing a ribose, 2'-deoxyribose, 2',3'-dideoxyribose, arabinose or other cleavable sugar portion, which may additionally contain a 2' or 3'-substituent such as halo, eg. chloro or fluoro; alkoxy; amino or thio. Specific examples of such nucleoside derivatives are 1-(b-D-arabinofuranosyl)-5-prop-1-ynyluracil; and 2',3'-dideoxy-5-ethynyl-3,-flourouridine. Compounds analogous to prodrugs of 5-FU as mentioned hereafter may in general be employed. References herein to uracil derivatives (or uracil reductase inactivators) include reference to prodrugs thereof.

Prodrugs of 5-fluorouracil (5-FU) are compounds which are metabolised in vivo to 5-fluorouracil and include 5-fluorouridine, 5-fluoro-2-deoxyuridine, 5-fluoro-2-deoxycytidine, 5'-deoxy-4',5-fluorouridine, 5'-deoxy-5-fluorouridine, 1-(2-tetrahydrofuranyl)-5-fluorouracil and 1-$C_{1-8}$ alkylcarbamoyl-5-fluorouracil derivatives.

5-FU or a prodrug thereof and the said 5-uracil derivative may be employed in combination in accordance with the invention by administration of the components of the combination to an appropriate subject either concomitantly, for example in a unitary pharmaceutical formulation; or, more preferably, separately or sequentially within a sufficient time period whereby the desired therapeutic effect of the combination is achieved. Preferably the 5-uracil derivative is administered first, and 5-FU or a prodrug thereof administered subsequently, advantageously from 15 mins to four days, usually 1 to 15 hours, especially 1 to 2 hours thereafter.

5-FU or a prodrug thereof and the 5-uracil derivative may be administered respectively for therapy by any suitable route including oral, rectal, nasal, topical (including buccal and sublingual), vaginal and parenteral (including subcutaneous, intramuscular, intravenous and intradermal).

It will be appreciated that the preferred route will vary with the condition and age of the recipient, the nature of the infection and other clinical factors.

Hitherto it has not been viable to administer 5-FU orally, as it is destroyed by uracil reductase in the gastro-intestinal tract. However, it has now been found that if a 5-substituted uracil derivative (as hereinbefore defined) is administered prior to oral administration of 5-FU (or a prodrug thereof), high and persistent levels of 5-FU are obtained in the plasma, indicating that this compound is not being destroyed. This is a further advantage of the present invention. Preferably the 5-FU is administered within 15 mins to four days, usually 1 to 15 hours, especially 1 to 2 hours of the 5-uracil derivative.

Normally, patients exhibit a high degree of variability in 5-FU plasma concentrations resulting from a given 5-FU dosage, which may be due to rates of 5-FU elimination which differ from patient to patient. There may also be diurnal variations within individual patients. The use of the 5-substituted uracil derivative according to the present invention is found to markedly reduce this subject-to-subject variability (see Experiment 3).

In general a suitable dose of 5-FU or a prodrug thereof will be in the range of 0.1 to 1000 mg per kilogram body weight of the recipient-per day, preferably in the range of 0.1 to 200 mg per kilogram body weight per day. If 5-FU itself is administered the dose is preferably in the range of 0.1 to 50 mg per kilogram body weight per day but higher doses of prodrugs of 5-FU may be administered. The dose of 5-FU or prodrug thereof may be administered in unit dosage forms, for example, containing 5 to 3000 mg, preferably 20 to 1000 mg, active ingredient per unit dosage form.

Experiments with 5-FU suggest that a dose should be administered to achieve peak plasma concentrations of the active compound of from about 0.01 to about 1.5 ug/ml.

The 5-uracil derivative may be administered in a dosage in the range of 0.01 to 50 mg per kilogram body weight of the recipient per day, particularly 0.01 to 10 mg/kg. The dose is more preferably in the range of 0.01 to 0.4 mg per kilogram body weight per day, depending on the derivative used. An alternative preferred administration regime is 0.5 to 10 mg/kg once per week.

The desired dose is preferably presented as one, two or more sub-doses administered at appropriate intervals throughout the day. These sub-doses may be administered in unit dosage forms for example containing 1 to 200 mg preferably 2 to 100 mg, more preferably 2 to 50 mg, of the 5-uracil derivative.

The uracil reductase inactivator and the 5-FU are usually employed in an appropriate ratio to substantially reduce the natural subsisting uracil reductase level in the subject. Such a ratio based on the respective weights of uracil reductase inactivator and 5-FU is generally in the range 1:0.01 to 1:100, preferably in the range 1:0.1 to 1:50, and particularly in the range 1:1 to 1:10.

5-FU or prodrug thereof and the 5-uracil derivative are preferably administered in a pharmaceutical formulation, either in a single pharmaceutical formulation containing both components or in separate administrations each containing one of the components of the combinations. The 5-uracil derivative will potentiate 5-FU, so that lower doses of 5-FU will be employed.

The present invention thus includes as a further feature a pharmaceutical formulation comprising a 5-uracil derivative as hereinbefore defined optionally in combination with 5-FU or a prodrug thereof together with at least one pharmaceutically acceptable carrier or excipient.

Each carrier must be "pharmaceutically acceptable" in the sense of being compatible with the other ingredients of the formulation and not injurious to the patient. Formulations include those adapted for oral, rectal, nasal, topical (including buccal and sublingual), vaginal and parenteral (including subcutaneous, intramuscular, intravenous and intradermal) administration. The formulations may conveniently be presented in unit dosage form and may be prepared by any methods well known in the art of pharmacy. Such methods include the step of bringing into association the active ingredient with the carrier which constitutes one or more accessory ingredients. In general, the formulations are prepared by uniformly and intimately bringing into association the active ingredient with liquid carriers or finely divided solid carriers or both, and then if necessary shaping the product.

Formulations of the present invention adapted for oral administration may be presented as discrete units such as capsules, cachets or tablets each containing a predetermined amount of the active ingredient; as a powder or granules; as a solution or a suspension in an aqueous or non-aqueous liquid; or as an oil-in-water liquid emulsion or a water-in-oil liquid emulsion. The active ingredient may also be presented as a bolus, electuary or paste. Oral administration is the preferred route.

A tablet may be made by compression or moulding, optionally with one or more accessory ingredients. Compressed tablets may be prepared by compressing in a suitable machine the active ingredient in a free-flowing form such as a powder or granules, optionally mixed with a binder (e.g. povidone, gelatin, hydroxypropylmethylcellulose), lubricant, inert diluent, preservative, disintegrant (eg. sodium starch glycollate, cross-linked povidone, cross-linked sodium caroxymethylcellulose) surface-active or dispersing agent. Moulded tablets may be made by moulding in a suitable machine a mixture of the powdered compound moistened with an inert liquid diluent. The tablets may optionally be coated or scored and may be formulated so as to provide controlled release of the active ingredient therein using, for example, hydroxypropylmethylcellulose in varying proportions to provide the desired release profile.

Formulations for topical administration in the mouth include lozenges comprising the active ingredient in a flavoured basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Formulations for rectal administration may be presented as a suppository with a suitable base comprising for example cocoa butter or a salicylate.

Formulation for vaginal administration may be presented as pessaries, tampons, creams, gels, pastes, foams or spray formulations containing in addition to the active ingredient such carriers as are known in the art to be appropriate.

Formulations for parenteral administration include aqueous and non-aqueous isotonic sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose sealed containers, for example, ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets of the kind previously described.

Liquid formulations including dissolved 5-uracil derivative are preferably buffered to a pH of 7 to 11, generally 9.5 to 10.5. Preferred unit dosage formulations are those containing a daily dose or unit, daily sub-dose, as hereinabove recited, or an appropriate fraction thereof, of an active ingredient.

The above-mentioned 5-uracil derivatives which are employed in combination with 5-fluorouracil or a prodrug thereof in accordance with the present invention may be prepared in conventional manner. For example, the inactivators referred to above may be prepared by the methods described in J. Heterocycl. Chem. 19(3) 463–4 (1982) for the preparation of 5-ethynyluracil; J.Chem. Soc. Perkin Trans. 1(16), 1665–70 (1981) for the preparation of 5-(2-bromovinyl)uracil, 5-bromoethynyluracil and 5-(2-bromo-1-chlorovinyl)uracil; Nucleic Acid Chemistry, Vol. 2, 927–30 (1978) for the preparation 5-cyano-uracil; Nucleic Acids Research, 1(1) 105–7 (1974) for the preparation of 5-vinyluracil; Z. Chem 17(11) 415–16 (1977) for the preparation of 5-trifluoromethyluracil; Nucleic Acids Research 3 (10), 2845 (1976) for the preparation of 5-(1-chlorovinyl) uracil.

The above prodrug nucleoside derivatives may also be prepared in conventional manner, for example in accordance with processes described in European Patent Specification No. 356166 for the preparation of 3'-fluoro-2', 3'-dideoxy-5-alkynyluridine compounds, such as 2',3'-dideoxy-5-ethynyl-3'-fluorouridine, and European Patent Specification No.272065 for the preparation of 5-alkynyluracil arabinosides, such as 1-(b-D-arabinofuranosyl)-5-prop-1-ynyluracil.

The novel 5-$C_{3-6}$ alkynyluracil compounds referred to above, which are preferred 5-uracil derivatives for use in accordance with the invention, may be prepared by one of the following processes, namely:

a) treatment of 5-$C_{3-6}$ alkynyluridine compound to effect conversion thereof to be desired uracil compound; or b) treatment of uracil compound substituted in the 5-position by an appropriate leaving group with a $C_{3-6}$ alkyne to give the desired uracil compound.

In the above process a), conversion may be effected by enzymatic means, for example by treatment of the uridine compound with a thymidine phosphorylase enzyme, advantageously in a buffered medium at a pH of 6 to 8.

In the above process b), a uracil compound substituted in the 5-position by a suitable leaving group e.g. iodo or bromo, is treated with a $C_{3-6}$ alkyne in the presence of an appropriate palladium catalyst such as bis (triphenylphosphine) palladium (II) chloride and cuprous iodide in an amine solvent such as triethylamine. The following Examples illustrate the present invention.

EXAMPLE 1

5-Propynyluracil

A) To a stirred solution of 2'-deoxy-5-propynyluridine (European Patent Specification No. 272065) (20 g, 75 mmol) in aqueous phosphate buffer at pH 6.84 (1250 mL) was added purified *E. coli* thymidine phosphorylase (10,000 units) (T. A. Krenitsky et al, Biochemistry, 20, 3615, 1981; U.S. Pat. No. 4,381,344) and alkaline phosphatase (10,000 units) [Sigma type VII-s from bovine intestinal mucosa] and the whole mixture was incubated at 37° C. for 24 hours. The resulting white precipitate was filtered, washed with water (3×100 mL), ethanol (2×100 mL), ether (2×100 mL) and dried in vacuo over phosphorus pentoxide to give the title compound.

M.pt.: 275–280° C. (dec.)

$^1$H nmr & ($d_6$DMSO) 11.5–11.0 (bs, 2H, NH), 7.61 (1H, s, H-6), 1.95 ppm (3H, s, $CH_3$)

Microanalysis calculated for $C_7H_6N_2O_2$: C, 56.00; H, 4.03; N, 18.66. Found: C, 55.92; H, 4.05; N, 18.77.

B) 1-Arabinofuranosyl-5-propynyluracil, (2.92 g, 20.4 mmoles), 200 ml aqueous potassium phosphate, pH 6,8 4,000 IU thymidine phosphorylase (Krenitsky, T. A. et al Biochemistry, 20,3615,1981 and U.S. Pat. No. 4,381,444), 4,000 IU uridine phosphorylase (Krenitsky, T. A. et al Biochemistry, 20,3615,1981 and U.S. Pat. No. 4,381,444) and 2,000 IU alkaline phosphatase (Boehringer Mannheim) were stirred at 40° C. for five days. Then 8,000 IU of thymidine phosphorylase, 20,000 IU uridine phosphorylase, 2,000 IU alkaline phosphatase and 30 IU acid phosphatase (Boehringer Mannheim) were added and incubation continued for an additional five days. 5-Propynyluracil, being less soluble than the nucleoside, precipitated from the reaction mixture.

The precipitate and liquid were dried in vacuo, then 5-propynyluracil was crystallized twice from hot water and vacuum dried at room temperature to give 0.92 g (6.1 mmoles) 5-propynyluracil in 59% yield.

$^1$H NMR & (dDMSO) 11.2 ppm (bs, 2H, 1H and 3H), 7.6 ppm (1H, s, 6H), 1.95 ppm (3H, s $CH_3$).

CHN calculated for $C_7H_6N_2O_2$: C, 56.00; H, 4.03; N, 18.66 Analyzed at: C, 55.95; H, 4.03; N, 18.60.

UV spectra: in 0.1 M HCl max at 287 nm and 231 nm; in 50 mM potassium phosphate, pH 7.0 max at 287 nm and 231 nm; in 0.1 M NaOH max at 306 nm and 240 nm.

Mass spectrum gave peak at molecular ion weight of 151.

EXAMPLE 2

(5-ethynyluracil (EU))

(a) 5-(Trimethylsilylethynyl)uracil

A solution of 5-iodouracil (8 g, 30 mmol) in redistilled triethylamine (500 mL) and dry DMF (10 mL) was degassed with oxygen-free nitrogen for 15 minutes. Bis (triphenylophosphine)palladium (II) chloride (0.5 g), copper (I) iodide (0.5 g) and trimethylsilylacetylene (10 g, 102 mmol) were then added and the mixture was heated with stirring at 50° C. for 24 hours. The cooled reaction mixture was filtered, the filtrate evaporated to dryness and the residue dissolved in dichloromethane (500 mL). The organic solution was washed with a 2% aqueous solution of disodium EDTA (3×250 mL), water (3×200 mL), dried ($Na_2SO_4$) and evaporated to dryness. The residue was triturated with ethanol to give the first crop of the title compound. The solid filtered from the reaction mixture was also found to contain the required product but in a more impure form and so was worked up as above in a separate batch to give a second crop.

$^1$H nmr & ($d_6$DMSO) 11.75–10.85 (2H, bs, NH), 7.75 (1H, s, H-6), 0.15 ppm (9H, m, $SiCH_3$).

(b) 5-Ethynyluracil

A solution of 5-(trimethylsilylethynyl)uracil (5.3 g, 24.4 mmol) in 0.2M solution of sodium methoxide in methanol (400 mL) was stirred at room temperature for 3 hours and neutralized to pH 7 with dilute hydrochloric acid. The precipitated product was filtered, washed with methanol and dried to give a first crop of the title compound. The filtrates and washings were combined, evaporated to dryness and the residue crystallised from methanol to give the second crop of product. Combination of both crops and a further recrystallisation from ethanol gave a pure product.

M.pt.: 260° C. (dec.)

$^1$H nmr & ($d_6$DMSO) 11.6–10.8 (2H, bs, NH), 7.8 (1H, s, H-6), 4.03 ppm (1H, s, acetylenic H)

Microanalysis calculated for $C_6H_4N_2O_2$: C, 52.95; H, 2.96; N, 20.58. Found: C, 52.04; H, 2.92: N, 20.3.

EXAMPLE 3

(5-ethynyluracil)

a) 2,4-Dimethoxy-5-iodo-pyrimidine

A dry 1 L round-bottomed flask was charged with 5-iodouracil (50 g, 0.21 mol), phosphorus oxychloride (300 ml), and N,N-diethylaniline (6 drops). The heterogenous mixture was heated in a 120° C. oil bath under a nitrogen atmosphere for 24 hours. The phosphorus oxychloride was distilled off (some product co-distills off). The reaction solution was next slowly and cautiously poured over ice (1 L) and solid sodium bicarbonate keeping the internal temperature at or below −20° C. (This was accomplished by cooling in a dry-ice acetone bath). once the addition was complete, the reaction mixture was adjusted to pH 7 by addition of solid sodium bicarbonate. The mixture was extracted with methylene chloride and the organic fractions dried by passage through phase separator paper. The crude solution of 2,4-dichloro-5-iodopyrimidine was immediately added dropwise to a solution containing MEOH (400 ml) and sodium methoxide (28.8 g, 0.533 mol). This addition took 1 hour. The reaction was then stirred at room temperature overnight. The solution was neutralized with $CO_2$(gas), extracted with methylene chloride, dried over anhydrous $Na_2SO_4$, filtered and concentrated. The crude product was adsorbed onto silica gel (100 g) and loaded onto a 400 g silica gel flash chromatography column. The column was eluted with 90:10 hexanes: ethyl acetate (v:v). The appropriate fractions were combined and concentrated to a white solid as the title compound.

Yield 26.7 g (48%)

200 MHZ NMR $CDCl_3$ &=3.97 (s, 3H); 4.02 (s, 3H), 8.43 (s,1H).

b) 2,-4-Dimethoxy-5-(b-trimethylsilyl)-ethynylpyrimidine

A dry 1 L round-bottomed flask under a nitrogen atmosphere was charged with the product of stage a) (26.7 g, 0.10 mol), dry methylene chloride (Aldrich, 150 mL), dry $Et_3N$ (freshly distilled from KOH pellets, 250 mL). The system was evacuated and purged with nitrogen several times via a Firestone valve. Trimethylsilylacetylene (21.2 mL, 0.15 mol; Aldrich) was added by syringe. Next were added bis(triphenylphosphine)palladium (II) chloride (Aldrich 5.84 g, 8.32 mmol) and copper (I) iodide (Aldrich 4.76 g, 25 mmol). The mixture was heated in a 60° C. oil bath for 2 hours, cooled and filtered through Celite. The filtrate was concentrated in vacuo. The residue was diluted with toluene (100 mL) and then the toluene was removed in vacuo. The residue was taken up into methylene chloride (200 mL), filtered and the filtrate extracted with 5% aq. ethylenediaminetetraacetic acid, disodium salt dihydrate (3×100 mL Aldrich), $H_2O$ (1×100 mL). The organic layer was dried via passage through phase separator paper and concentrated in vacuo. The product was purified on a Waters Prep 500 eluting with 95:5 hexanes: ethyl acetate (v:v). The crude product was adsorbed onto 100 g of silica gel and loaded onto a 400 g silica gel flash chromatography column. The column was eluted with 97.5:2.5 hexanes: ethyl acetate (v:v). The appropriate fractions were combined and concentrated.

Yield 16.94 g (73%).

A 1.2 g sample of the resulting compound was bound to 6 g of silica gel and loaded onto a 50 g flash chromatography column. The column was eluted with hexanes: ethyl acetate 95:5 (v:v). The appropriate fractions were combined, concentrated, stripped with $CH_2Cl_2$ (2×30 mL), and dried in vacuo to yield 1.000 g of the title compound, m.p. 72.5–73° C.

Lit. m.p. 73–74° C. J. Heterocyclic Chem., 19, 463 (1982).

c) 5-(b-trimethylsilyl)ethynyluracil

A dry 3-necked round-bottomed flask under nitrogen was charged with 2,4-dimethoxy-5-(b-trimethylsilyl) ethynylpyrimidine (6.5 g, 27.5 mmol), dry acetonitrile (120 mL Aldrich), sodium iodide (oven dried in vacuo 80° C., 18 h, 12.4 g, 82.7 mmol) and chlorotrimethylsilane (10.5 mL, 82.7 mmol freshly distilled). The mixture was heated at reflux for 3 hours and then concentrated in vacuo. The residue was digested with a solution containing methanol (40 mL) and water (20 ML) and the product filtered off to give 1.48 g (26%). The product was dissolved in chloroform and the solution adsorbed onto silica gel 7 g) which was then loaded onto a 35 g silica gel flash chromatography column. Elution with chloroform:methanol 95:5 (v:v) followed by chloroform:methanol 90:10 (v:v) and evaporation of the product-containing fractions yielded 1.23 g of the title compound as a white solid.

d) 5-Ethynyluracil

A solution containing 5-(b-trimethylsilyl)ethynyluracil (3.85 g, 18.4 mmol) and methanol (370 mL) was treated with a second solution containing sodium hydroxide (2.3 g, 57.5 mmol) and water (18 mL). The mixture was stirred at room temperature for 2 hours and then concentrated in vacuo. The residue was suspended in water (35 mL) and the pH adjusted to 5 using 0.1 N HCl. The solids dissolved and then a second precipitate formed when the pH-5. The product was filtered, washed with $H_2O$, and then dried in vacuo to give 2.3 g (92%) of 5-ethynyluracil as a light beige powder.

Microanalysis calculated for $C_6H_4N_2O_2$: C, 52.95: H, 2.96; N, 20.58. Found: C, 52.79; H, 3.02; N, 20.44.

EXAMPLE 4

(5-ethynyluridine)

a) 2',3'-5'-Tri-O-Acetyl-5-iodouridine

A dry 250 mL round-bottomed flask was charged with 5-iodouridine (10 g, 27 mmol Aldrich), anhydrous pyridine (30 mL) and acetic anhydride (30 mL). The reaction was stirred at room temperature for 30 minutes under a nitrogen atmosphere and the solvent removed in vacuo. The compound was diluted with toluene (2×50 mL) and the toluene removed in vacuo. The product was purified on a 75 g flash chromatography column which was eluted with 90:10 (v:v) $CHCl_3$:MeOH. The appropriate fractions were combined and concentrated to give the title compound as a white foam. This was used directly in the next stage.

b) 2',3',5'-Tri-O-Acetyl-5-[2-(trimethylsilyl)ethvnyl]uridine

A dry 1 L round-bottomed flask equipped with a reflux condenser (under $N_2$ atmosphere) was charged with the product of stage a) (27 mmol), dry methylene chloride (260 mL, Aldrich) and dry triethylamine (260 mL. freshly distilled from NaOH pellets). The system was evacuated and purged with nitrogen several times and remained under a nitrogen atmosphere. Next was added (trimethylsilyl) acetylene (11.65 mL, 82 mmol; Aldrich) followed by copper (I) iodide (Aldrich, 1.57 g, 8.2 mmol) and bis (triphenylphosphine)palladium II chloride (Aldrich, 1.85 g, 2.6 mmol). The mixture was heated in a 60° C. oil bath for 30 minutes, cooled, and filtered. The filtrate was concentrated in vacua. The residue was taken up into $CH_2Cl_2$ (300 mL), filtered, washed with 5% aq. ethylenediaminetetraacetic acid, disodium salt (2×75 mL), $H_2O$ (100 mL), dried over $Na_2SO_4$, filtered and concentrated in vacuo.

The resulting compound was bound to 50 g of silica gel and loaded onto a 400 g silica gel flash chromatography column which was eluted with $CHCl_3$. The product fractions were combined and concentrated to yield the title compound as light yellow foam.

Yield 13 g

300 MHz NMR $CDCl_3$ & 8.2 (br s, NH, 1H), 7.77 (s, 1H, H6), 6.11 (d, H1',1H), 2.22 (s, 3H, OAc), 2.13 (s,3H OAc), 2.11 (s, 3H, OAc), 0.22 (s, 9H, $SiMe_3$).

c) 5-Ethynyluridine

The product of stage b) (9.5 g, 24 mmol) was dissolved in methanol (200 mL) and diluted with a solution containing sodium (0.8 g) and methanol (100 mL). The reaction was stirred at room temperature for 2 hours and was then neutralized using Dowex 50W-X8 (H+ form) resin. The resin was removed by filtering and washed with methanol. The filtrate was concentrated in vacuo to give 4.85 g of a beige solid. The compound was purified an a Waters Prep 500 reverse phase $C_{18}$ column which was eluted with $H_2O$/MeOH 85:15 (v:v) to give 1.2 g of the title product (white solid). Impure fractions were re-chromatographed. An additional 1.94 g of product were obtained.

Yield 49%

| Calculated: | % C, 49.25 | % H, 4.47 | % N, 10.44 |
|---|---|---|---|
| Found: | % C, 49.07 | % H, 4.53 | % N, 10.32 |

200 MHz NMR (DMSOd$_6$) & 11.60 (br s, NH, 1H), 8.36 (s, H6,1H), 5.72 (d, J=4.3 Hz H1', 1H), 4.01 (s, 1H, C=C—H).

The following Examples illustrate pharmaceutical formulations in which the "Active Ingredient" is 5-propynyluracil, 5-ethynyluracil or other uracil reductase inactivator as mentioned above; or mixtures thereof with 5-fluorouracil.

EXAMPLE 5

Tablet Formulations

The following formulations 5A, 5B and 5C are prepared by wet granulation of the ingredients (except the magnesium stearate) with a solution of the povidone followed by drying of the granules, addition of the magnesium stearate and compression.

| | mg/tablet | mg/tablet |
|---|---|---|
| Formulation 5A | | |
| Active ingredient | 5 | 2 |
| Lactose, B.P. | 205 | 75 |
| Povidone, B.P. | 15 | 10 |
| Sodium starch glycollate | 20 | 10 |
| Magnesium stearate | 5 | 3 |
| | 250 | 100 |
| Formulation 5B | | |
| Active ingredient | 5 | 2 |
| Lactose, B.P. | 155 | — |
| Avicel PH 101 | 50 | 25 |
| Povidone, B.P. | 15 | 10 |
| Sodium starch glycollate | 20 | 10 |
| Magnesium stearate | 5 | 3 |
| | 250 | 50 |
| Formulation 5C | | |
| Active ingredient | 5 | |
| Lactose, B.P. | 205 | |
| Starch | 50 | |
| Povidone, B.P. | 6 | |
| Magnesium stearate | 4 | |
| | 270 | |

The following formulation 5D was prepared by direct compression of the admixed ingredients. The lactose used is of the direct compression type.

| Formulation 5D | mg/tablet |
|---|---|
| Active ingredient | 5 |
| Lactose | 155 |
| Avicel PH 101 | 100 |
| | 260 |

The following formulation 5E is a controlled release tablet and is prepared by wet granulation of the ingredients (except magnesium stearate) with a solution of the pavidone, followed by drying of the granules, addition of the magnesium stearate and compression.

| Formulation 5E | mg/tablet |
|---|---|
| Active ingredient | 5 |
| Hydroxypropylmethylcellulose (Methocel K4M Premium) | 110 |
| Lactose, B.P. | 50 |
| Povidone, B.P. | 28 |
| Magnesium stearate | 7 |
| | 200 |

EXAMPLE 6

Capsule Formulations

The following formulations 6A and 6B are prepared by admixing the uncompressed ingredients and filling into a two-part hard gelatin capsule.

| | mg/capsule |
|---|---|
| Formulation 6A | |
| Active ingredient | 10 |
| Lactose, B.P. | 250 |
| Sodium starch glycollate | 25 |
| Magnesium stearate | 5 |
| | 290 |
| Formulation 6B | |
| Active ingredient | 5 |
| Pregelatinized starch NF15 | 245 |
| | 250 |
| Formulation 6C | |
| Active ingredient | 10 |
| Macrogol 4000, B.P. | 340 |
| | 350 |

The Macrogol 4000, B.P. is melted and the active ingredient dispersed therein. The thoroughly mixed melt is then filled into a two-part hard gelatin capsule.

EXAMPLE 7

| Injectable Formulation | |
|---|---|
| Active ingredient | 10 mg |
| Sterile, pyrogen free pyrophosphate buffer (pH 10), q.s. to | 10 ml |

The active ingredient is dissolved in most of the phosphate buffer (35–40° C.), then made up to volume and filtered through a sterile micropore filter into a 10 ml amber glass vial (type 1) and sealed with a sterile closure and overseal.

EXAMPLE 8

| Suppository Formulation | mg/suppository |
|---|---|
| Active ingredient, 63um* | 10 |
| Hard fat, B.P. (Witepsol H15-Dynamit Noble 1) | 1790 |
| | 1800 |

*The active ingredient is used as a powder wherein at least 90% of the particles are of 63 um or less.

Our-fifth of the Witepsol H15 is melted in a steam-jacketed pan at 45° C. maximum. The active ingredient is sifted through a 200 um sieve and added to the molten base with mixing, using a silverson fitted with a cutting head, until a smooth dispersion is achieved. Maintaining the mixture at 45° C., the remaining Witepsol HIS is added to the suspension and stirred to ensure a homogeneous mix. The entire suspension is passed through a 250 um stainless steel screen and, with continuous stirring, is allowed to cool to about 40° C. At a temperature of 38° C. to 40° C. 1.80 g of the mixture is filled into suitable plastic moulds. The suppositories are allowed to cool to room temperature.

Certain Experiments were carried out into the effectiveness of 5-substituted uracils according to the invention.

Experiment 1

Determination of Uracil Reductase Inactivation

Uracil reductase (1 micromolar) (dihydropyrimidine dehydrogenase, $EC_{1.3.1.2}$) purified from bovine liver was incubated with 100 micromolar inactivator and 5 mM dithiothreitol (enzyme reductant) at 37° for 30 minutes in 0.05 M Tris-HCl at pH 8.0. The enzyme and inactivator were diluted 100-fold into the assay buffer, which contained 200 micromolar NADPH, 200 micromolar thymine and lm dithiothreitol in Tris-HCl at pH 8.0. The velocity of the enzyme was determined spectrophotometrically. These velocities have been corrected for NADPH oxidase activity, which was less than 10% of the rate of thymine-dependent oxidation of NADPH. The % inactivation of the enzyme was equal to 100% minus the percent of enzymatic activity remaining. Enzyme incubated without inhibitor was stable under these conditions. Parenthetical values are the relative first-order rate constants for inactivation of enzyme determined from similar experiments where the fractional activity was measured as a function of the time of incubation of 50 micromol inactivator with enzyme.

The results are given below:

| Compound | % Inactivation | |
|---|---|---|
| 5-ethynyluracil | 100 | (100) |
| 5-cyanouracil[a] | 100 | (14) |
| 5-propynyluracil | 100 | (8) |
| 5-bromoethynyluracil | 100 | (8) |
| 5-(1-chlorovinyl)uracil | 100 | (5) |
| 5-iodouracil | 100 | (4) |
| 5-hex-1-ynyluracil[a] | 90 | |
| 5-vinyluracil[a,b] | 86 | |
| 5-trifluoromethyluracil | 75 | |
| 5-bromouracil | 75 | |

[a]The inhibition was reversible since enzyme treated with this derivative slowly regained activity after a 100-fold dilution into the assay mixture.
[b]These nucleobases were generated in situ by treating the respective nucleosides with 40 units/ml of thymidine phosphorylase in 35 mM potassium phosphate for 20 minutes prior to addition to uracil reductase. The parent nucleosides were not inactivators.

Figure 1:
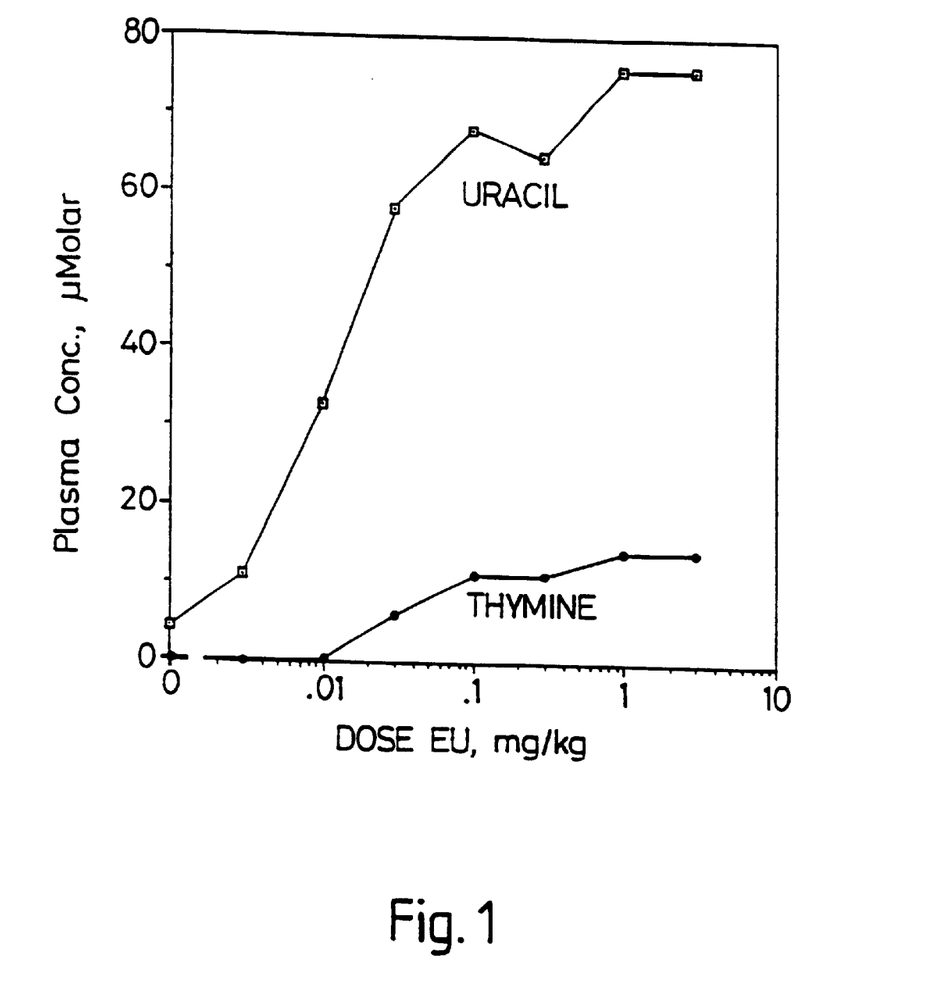
FIG. 1—shows increased levels of uracil and thymine at a time of four hours following various oral EU doses in rats.
Figure 2:
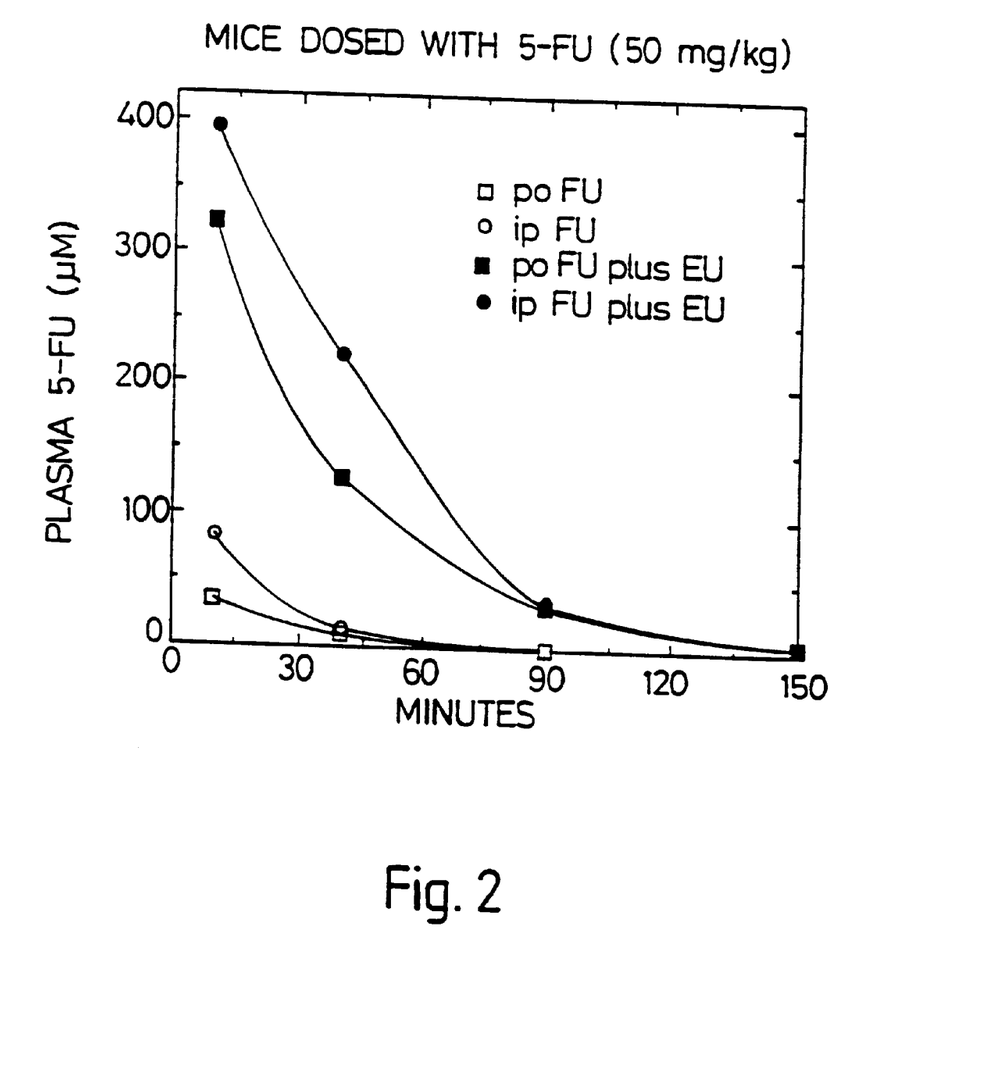
FIG. 2—shows that EU increased plasma levels of 5-fluorouracil (5-FU). Mice were dosed either orally (p.o.) or interperitoneally (i.p.) with 5-FU. 5-ethynyluracil (EU) at 2 mg/kg was dosed i.p. 90 minutes prior to the 5-FU.

The effectiveness of 5-ethynyluracil (EU) was investigated and is reported in the following Experiments 2 to 4 and Figures wherein FIG. 1 shows increased levels of uracil and thymine at a time of four hours following various oral EU doses in rats; and FIG. 2 shows that EU increased plasma levels of 5-fluorouracil (5-FU). Mice were dosed either orally (p.o.) or interperitoneally (i.p.) with 5-FU. 5-ethynyluracil (EU) at 2 mg/kg was dosed i.p. 90 minutes prior to the 5-FU.

Experiment 2

Inactivation of uracil reductase (in vivo)

Mice, rats, dogs and monkeys dosed with small amounts of 5-ethynyluracil (EU) rapidly developed greatly elevated plasma uracil and thymine levels. The maximum effect occurred at about 0.1 mg/kg p.o. in rats, at 0.5 to 1 mg/kg s.c. in mice, and at approximately 1 mg/kg intravenously (i.v.) in dogs and probably represents total inactivation of uracil reductase. These doses elevated mouse, dog, and rat plasma uracil from about 3 uM to about 50–60 uM. Plasma uracil decreased to normal over 24 hr (half-life=10 hr). FIG. 1 shows the increased plasma levels of uracil and thymine in the rat at a time of 4 hours following various oral doses of 5-ethynyluracil, due to inactivation of uracil ieductase. The $ED_{50}$ equals 0.01 mg/kg.

Experiment 3

Effect on plasma-FU level

Mice and rats pretreated with 5-ethynyluracil (EU) and then dosed with FU sustained higher plasma levels of FU than mice not pretreated (FIG. 2). In addition, the usual variability in plasma FU in rats orally dosed with FU at 50 mg/kg was eliminated by EU pretreatment. The AUC of the plasma FU concentration-time curves were 41, 126 and 68 (ave=78±55%) versus 417, 446 and 426 (ave=430±3%) for nonpretreated and EU pretreated rats, respectively.

Experiment 4

Potentiation of the antitumor activity of 5-fluorouracil (5-FU) in mice by 5-Ethynyluracil (EU).

Colon 38 tumor was implanted in mice on day zero. Mice (8 per group) were treated with 5-FU on days one through nine with the doses indicated in Table 2 EU was dosed i.p. at 2 mg/kg 30 minutes prior to 5-FU dosing where indicated.

TABLE 2

% Mice Tumor Free on Day 17

| Dose 5-FU (mg/kg) | FU i.p. plus EU | FU i.p. | FU p.o. plus EU | FU p.o. |
|---|---|---|---|---|
| 0.25 | 0 | | | |
| 0.5 | 25 | | 0 | |
| 1 | 12.5 | | 25 | |
| 2 | 37.5 | | 37.5[a] | |
| 3 | 100 | | | |
| 4 | 100 | | | |
| 10 | | 0 | | 0 |
| 15 | | 12.5 | | 12.5 |
| 20 | | 12.5 | | 12.5 |
| 25 | | — | | 12.5 |
| 30 | | 87.5[a] | | 12.5 |

[a]One non-tumor related death occurred in these groups

What is claimed is:

1. A pharmaceutical composition which comprises a compound selected from a 5-substituted- or 5,6,-dihydro-5-substituted-uracil wherein said 5-substituent is halo-substituted-$C_{1-4}$ alkyl, $C_{2-6}$ alkenyl, 1-halo-$C_{2-6}$ alkenyl, $C_{2-6}$ alkynyl, halo-substituted-$C_{2-6}$ alkynyl or a prodrug thereof wherein said prodrug comprises a nucleoside analog of ribose, 2'-deoxyribose, 2',3'-dideoxyribose, or arabinose each optionally substituted with halo, alkoxy, amino, or thio and wherein the pharmaceutical composition further comprises 5-fluorouracil or a nucleoside of 5-fluorouracil capable of being metabolized in vivo to 5-fluorouracil and a pharmaceutically acceptable carrier.

2. A pharmaceutical composition according to claim 1 in unit dosage form comprising 1 to 200 mg of said compound or said prodrug thereof.

3. A pharmaceutical composition according to claim 1 in unit dosage form comprising 5 to 3000 mg of 5-fluorouracil or a nucleoside of 5-fluorouracil capable of being metabolized in vivo to 5-fluorouracil.

4. A pharmaceutical composition according to claim 2 comprising 5 to 3000 mg of 5-fluorouracil or a nucleoside of 5-fluorouracil capable of being metabolized in vivo to 5-fluorouracil.

5. A pharmaceutical composition according to claim 2 which is adapted for oral administration.

6. A pharmaceutical composition comprising as separate or mixed components a compound selected from a 5-substituted- or 5,6,-dihydro-5-substituted-uracil wherein said 5-substituent is halo-substituted-$C_{1-4}$ alkyl, $C_{2-6}$ alkenyl, 1-halo-$C_{2-6}$ alkenyl, $C_{2-6}$ alkynyl, halo-substituted-$C_{2-6}$ alkynyl or a prodrug thereof wherein said prodrug comprises a nucleoside analog of ribose, 2'-deoxyribose, 2',3'-dideoxyribose, or arabinose each optionally substituted with halo, alkoxy, amino, or thio and wherein the pharmaceutical composition further comprises 5-fluorouracil or a nucleoside of 5-fluorouracil capable of being metabolized in vivo to 5-fluorouracil and a pharmaceutically acceptable carrier.

7. A pharmaceutical composition according to claim 6 wherein the ratio of said compound or said prodrug thereof to said 5-fluorouracil or said nucleoside of 5-fluorouracil capable of being metabolized in vivo to 5-fluorouracil is in the range 1:0.01 to 1:100 by weight.

8. A pharmaceutical composition according to claim 2 which is adapted for oral administration.

9. The pharmaceutical composition according to claim 6 which is adapted for oral administration.

10. The pharmaceutical composition according to claim 7 which is adapted for oral administration.

11. The pharmaceutical composition according to claim 8 which is a tablet or capsule.

12. The pharmaceutical composition according to claim 9 which is a tablet or capsule.

13. The pharmaceutical composition of claim 6 wherein the components are mixed.

14. The pharmaceutical composition of claim 13 comprising 5-ethynyl uracil and 5-fluorouracil.

15. The pharmaceutical composition of claim 14 wherein the ratio of 5-ethynyl uracil to 5-fluorouracil is 1:0.001 to 1:100.

16. The pharmaceutical composition of claim 14 wherein the ratio of 5-ethynyl uracil to 5-fluorouracil is 1:0.1 to 1:50.

17. The pharmaceutical composition of claim 15 comprising 1–200 mg of 5-ethynyl uracil.

18. The pharmaceutical composition of claim 15 comprising 2–100 mg of 5-ethynyl uracil.

19. The pharmaceutical composition of claim 15 comprising 2–50 mg of 5-ethynyl uracil.

* * * * *

UNITED STATES PATENT AND TRADEMARK OFFICE
CERTIFICATE OF CORRECTION

PATENT NO.    : 6,268,374 B1
DATED         : July 31, 2001
INVENTOR(S)   : Thomas Spector et al.

It is certified that error appears in the above-identified patent and that said Letters Patent is hereby corrected as shown below:

<u>Column 1,</u>
Lines 1-3, delete "This is a continuation of application Ser. No. 08/718,481 filed Sept. 26, 1996, which is a 371 of International application No.: PCT/FP95/00900, filed Mar. 9, 1995."

Signed and Sealed this

Tenth Day of December, 2002

JAMES E. ROGAN
*Director of the United States Patent and Trademark Office*